United States Patent [19]

Ahnell

[11] 4,220,715
[45] Sep. 2, 1980

[54] APPARATUS FOR AND METHOD OF DETECTION OF SIGNIFICANT BACTERIURIA IN URINE SAMPLES THROUGH MEASUREMENT OF HEAD SPACE GAS OXYGEN CONSUMPTION IN A CLOSED-VIAL SYSTEM

[75] Inventor: Joseph E. Ahnell, Hydes, Md.

[73] Assignee: Johnston Laboratories, Inc., Cockeysville, Md.

[21] Appl. No.: 930,680

[22] Filed: Aug. 3, 1978

[51] Int. Cl.² .................. C12Q 1/04; C12Q 1/06; C12M 1/34
[52] U.S. Cl. .................. 435/34; 23/230 B; 435/38; 435/39; 435/289; 435/291; 435/316
[58] Field of Search ............ 195/103.5 R, 103.5 M; 23/230 B; 422/80, 81; 195/127, 139; 435/29, 30, 31, 32, 33, 34, 35, 36, 37, 38, 39, 40, 291, 287, 316, 807, 289

[56] References Cited
U.S. PATENT DOCUMENTS

| | | | |
|---|---|---|---|
| 3,348,409 | 10/1967 | Arthur | 73/19 |
| 3,676,679 | 7/1972 | Waters | 195/127 X |
| 3,740,320 | 6/1973 | Arthur | 195/103.5 R |
| 3,861,195 | 1/1975 | von Hagan | 73/23 |
| 3,935,073 | 1/1976 | Waters | 195/103.5 R |
| 3,941,660 | 3/1976 | Mirsky | 195/139 X |
| 3,950,227 | 4/1976 | Efthymiou | 195/103.5 R X |
| 4,009,078 | 2/1977 | Wilkins et al. | 195/103.5 R |
| 4,073,691 | 2/1978 | Ahnell et al. | 195/103.5 M |
| 4,152,213 | 5/1979 | Ahnell | 195/127 X |

OTHER PUBLICATIONS

Abstracts of the Annual Meeting of the American Society for Microbiology, Abstracts M156 and M157; 1973.

*Primary Examiner*—Robert J. Warden
*Attorney, Agent, or Firm*—Schuyler, Birch, McKie & Beckett

[57] ABSTRACT

The detection of "significant bacteriuria" in a urine sample is accomplished by measuring the head space gas oxygen consumption in a closed vial system. A sample to be tested is introduced into a sealed vial containing a growth medium and the head space gas oxygen concentration initially measured. After a suitable incubation period, the oxygen concentration above the sample is again measured using a closed sample loop. A decrease in the head space oxygen concentration below a predetermined level indicates the presence of a significant quantity of oxygen consuming microorganisms in the sample.

28 Claims, 15 Drawing Figures

HEAD SPACE GAS OXYGEN CONTENT AS A FUNCTION OF INCUBATION TIME FOR VARIOUS VIAL SIZES AND SOLUTION VOLUMES.

HEAD SPACE GAS OXYGEN CONTENT AS A FUNCTION OF INCUBATION TIME FOR THE ORGANISM E.COLI

HEAD SPACE GAS OXYGEN CONTENT AS A FUNCTION OF INCUBATION TIME FOR THE ORGANISM E. CLOACAE

HEAD SPACE GAS OXYGEN CONTENT AS A FUNCTION OF INCUBATION TIME FOR THE ORGANISM P. MIRABILIS

HEAD SPACE GAS OXYGEN CONTENT AS A FUNCTION OF INCUBATION TIME FOR THE ORGANISM P. AERUGINOSA

HEAD SPACE GAS OXYGEN CONTENT AS A FUNCTION OF INCUBATION TIME FOR THE ORGANISM S. AREUS

HEAD SPACE GAS OXYGEN CONTENT AS A FUNCTION OF
INCUBATION TIME FOR THE ORGANISM C. ALBICANS

APPARATUS FOR AND METHOD OF DETECTION OF SIGNIFICANT BACTERIURIA IN URINE SAMPLES THROUGH MEASUREMENT OF HEAD SPACE GAS OXYGEN CONSUMPTION IN A CLOSED-VIAL SYSTEM

BACKGROUND OF THE INVENTION

1. Field of the Invention

The present invention relates to a method and apparatus for the initial screening of urine samples for significant bacteriuria.

2. Description of the Prior Art

One of the major problems confronting hospitals today is the accurate detection of urinary tract infections. The presence of bacteria in urine is termed bacteriuria. While urine in the bladder is ordinarily sterile, clean voided urine from normal individuals generally contains microorganisms that are indigenous residents of the urethra. The presence of any bacteria in the bladder or upper urinary tract is considered abnormal. Significant bacteriuria is a term indicating that the number of bacteria in the voided urine exceeds the numbers usually due to contamination from the anterior urethra. Commonly, this number is on the order of greater than 100,000 colony forming units (cfu) per milliliter of clean-caught voided urine.

Prior art methods for the detection of microorganisms present in various sources which include aqueous media such as blood, plasma, urine samples and the like are generally divided into two classes. In the first class are screening tests to determine whether or not large numbers of microorganisms are present in the sample. If a positive test is obtained by the first step, a second level of testing is employed to determine the type and amount of organism present. The most common method of estimation of microorganism population is accomplished by the nutrient agar plating technique in which a microorganism is allowed to grow on an agar nutrient substrate, and the growth of the microorganism is observed, at first visually and thereafter by microscopic examination. This technique, which is most commonly used clinically, requires overnight incubation of plates before results are available. Additional time may be required to perform biochemical tests and antibiotic susceptibilities.

Another technique for the determination of microorganisms involves supplying a microorganism in a growth medium with carbon-14 labeled glucose or the like. See Waters U.S. Pat. No. 3,676,679, Waters U.S. Pat. No. 3,935,073 and Mirsky U.S. Pat. No. 3,941,660. The microorganism metabolizes the radioactive glucose and evolves $C^{14}O_2$, which is sampled and counted. This technique has recently been suggested for use in urine sample screening tests for significant bacteriuria. See American Society for Microbiology, Abstracts M 156 and M 157 (1973). While positive results can be obtained by this method in a relatively short period of time, this method requires the use of comparatively expensive and complex apparatus and involves handling radioactive materials.

The prior art also describes a technique for detecting the presence of biologically active agents by analyzing for changes in composition of the culture gas over a sample in a closed vial. See Ahnell et al U.S. Pat. No. 4,073,641. This patent describes a system which uses mass spectrometry or gas chromatography to measure the ratio of a gaseous metabolic product such as $CO_2$ to a constant gas such as argon. A closed loop system is not disclosed in this patent. Among the gaseous metabolic products in the culture gas that Ahnell et al indicate can be monitored is oxygen.

Another technique described in the prior art is the Warburg-type respirometer. See e.g., VonHagen U.S. Pat. No. 3,861,195 and Arthur U.S. Pat. No. 3,348,409. This technique employs a complex apparatus in which each sample vial is associated with the measurement apparatus and communicates with a manometer for measuring the oxygen partial pressure of metabolically consumed oxygen over a bacteria sample. The Warburg technique further requires the absorption of metabolically generated $CO_2$ in order to obtain meaningful oxygen consumption data. This technique is also sensitive to barometric pressure requiring that an adjustment be made to the manometer connected to each vial, or else requiring that a reference vial be used in conjunction with each sample vial.

Another type of prior art detection technique which measures oxygen consumption employs the Clark-type polarographic oxygen electrodes for the measurement of dissolved oxygen. Typically, this technique employs two such oxygen electrodes to measure oxygen uptake or evolution by biological material in two separate cells. Results are given in terms of percentage oxygen saturation of the solution. Polarographic electrode measurements suffer from the disadvantage that the use of very thin oxygen-permeable membranes, usually polytetrafluoroethylene, are required to isolate the sample solution from contact with the electrode solution. These membranes require replacement about once a week in routine use. Moreover, the active area of the oxygen electrode must necessarily be submerged in the suspect sample in order to take a reading, making the testing of a plurality of samples with a single electrode extremely cumbersome if cross contamination of the samples is to be avoided. The electrode surfaces would necessarily have to be sterilized between samples using a strong bactericide, then rinsed completely with a sterile rinse solution so as not to kill organisms in or contaminate the contents of the next vial tested. Relatively high unit cost of such electrodes precludes the use of a separate electrode for each sample if more than a few samples are to be tested. In addition, all oxygen-sensitive electrodes require that samples be agitated or preferably stirred in a constant reproducible manner in order to produce accurate readings. Moreover, essentially all externally powered oxygen electrodes contain a platinum cathode and a silver anode maintained at a potential difference of about 0.8 V. As a consequence, any gases which may be reduced at this potential interfere with the measurement. Such gases are the halogens and sulfur dioxide, etc. The electrode is readily poisoned by gases which react with the silver anode, such as hydrogen sulfide ($H_2S$). Because $H_2S$ is readily produced by some bacteria which cause bacteriuria (most notably Proteus,sp.) in carbohydrate deficient, oxygen deficient media containing protein, possibility of poisoning such an electrode could occur while testing a first-morning, Proteus-positive urine.

A dissolved oxygen electrode based on the Galvanic principle is also known in the prior art. This electrode uses a lead-potassium hydroxide-silver cell to generate an emf proportional to oxygen partial pressure in solution. It too requires sample agitation for proper operation; a sample flow of at least one foot per minute past the membrane is recommended. It is probably equally sensitive to poisoning by $H_2S$.

Arthur U.S. Pat. No. 3,740,320 discloses an apparatus and method for measuring the amount of gas absorbed or released by a substance. Described as useful in water pollution control and waste management, the Arthur apparatus employs an aeration chamber for receiving a waste water sample containing pollution and bacteria. The aeration chamber is equipped with a liquid recirculation loop which is said to aid in aeration, and a gas recirculation loop which removes the gas above the liquid, subjects it to oxygen analysis (e.g., by paramagnetic analysis), and returns the gas via a diffuser to the body of the liquid. The Arthur apparatus is not designed nor could it be employed to determine the presence of a threshhold quantity of an oxygen-consuming microorganism in a small sample of a body fluid such as urine. Arthur is concerned primarily with measuring the quantity of bacterial food, i.e., sewage in a wastewater or activated sludge sample. Aerobic organisms responsible for oxygen demand will usually be present in very large numbers in such samples. If it is desired to determine the Biochemical Oxygen Demand (BOD) of wastewater having low bacterial count, the sample is normally seeded to introduce into the sample a biological population capable of oxidizing the organic matter in the wastewater.[1] When measuring the oxygen demand of a bacterial culture grown in batch mode, the organisms will also be present in high count, and the oxygen demand arising from their metabolism is employed by Arthur to monitor metabolic activity in the batch or to adjust process variables. No provision is made to insure sample-to-sample sterility, since the disclosed applications of the apparatus impose no sterility requirement.

[1] Standard Methods for the Examination of Water and Wastewater, American Public Health Assoc., Washington, D.C. (1971) p. 490.

The Arthur apparatus is thus most suitable in relatively large volume (500 cc and above) situations where oxygen-consuming bacteria are in excess and the nutrient value (BOD) of the sample is in question, or in situations where a high-volume biological process employing a relatively heavy bacterial suspension is to be monitored or controlled. These situations are in marked contrast to the process of the instant invention, which seeks to detect the presence of a threshold quantity of aerobic microorganisms ($10^5$/ml) in a small sample (8 cc total liquid volume) of excess nutient enclosed in a container volume less than 30 cc in the preferred embodiment, to be used in urine screening situations where sample-to-sample sterility must be maintained for all samples tested.

It is well known that sparging a liquid sample with circulated gas while agitating the liquid is an extremely efficient means of providing gas-liquid exchange. It would thus not be expected by one skilled in the art that the apparatus and method of Arthur, employing comparatively large volumes of sample sparged with circulated gas and bathed with circulated liquid, could be reduced greatly in volume while eliminating continuous circulation of the gas and liquid, and yet produce the required sensitivity and stability to detect a threshold quantity of microorganisms as in the instant invention.

From the foregoing it is clear that a rapid and automatic method for the detection of threshold quantities of microorganisms in the screening of urine samples for significant numbers of bacteria, would afford the laboratory considerable savings in time and effort. Rapid identification of the positive samples would permit biochemical and antimicrobial testing to begin sooner. Elimination of negatives from further consideration would remove about 80% of the total urine sample test load.

SUMMARY OF THE INVENTION

Accordingly, one object of the present invention is to provide a method of screening for significant bacteriuria which obviates the problems of prior art techniques.

It is also an object of the present invention to provide a detection technique which can be rapidly performed in a reliable manner utilizing inexpensive apparatus and materials.

It is another object of the present invention to provide a detection technique which is simple, easy to use and which can handle a plurality of samples.

It is also an object of the present invention to provide a method which can be fully automated if desired.

In accordance with these and other objectives, the present invention provides a method for detecting a threshold quantity of oxygen consuming microorganisms in a urine sample comprising the steps of:

(a) providing a sealable, sterile container containing a sterile culture medium capable of supporting growth of microorganism found in urine samples;

(b) introducing a sample to be tested into said container and sealing said container, the volume above said sample and medium defining a head space, and the gas initially filling this head space having a known oxygen concentration;

(c) subjecting said sealed container and its contents to conditions conducive to microorganism growth for a period of time sufficient for the growth of oxygen consuming microorganisms;

(d) withdrawing a portion of the head space gas from said container and causing the withdrawn gas to flow through a closed sampling loop which returns the withdrawn gas to the head space in the container; and (e) subjecting the gas flowing through the closed sampling loop to analysis for oxygen concentration, a drop in oxygen concentration below a predetermined level indicating the presence of a threshold quantity of said oxygen consuming microorganisms.

The present invention also provides apparatus for detecting oxygen-consuming microorganisms in a urine sample comprising:

(a) a sealable, sterile container adapted to hold in a lower portion thereof a sample of material to be tested and a culture medium which will support growth of the microorganism to be detected, said container also having an upper portion defining a head space for holding gas in contact with said sample and medium, said container further provided with means through which said sample can be introduced into said container;

(b) means for subjecting said container and its contents to conditions conducive to microorganism growth;

(c) means for withdrawing gas from the head space in said container;

(d) a sampling conduit communicating with said means for withdrawing gas;

(e) means communicating with said sampling conduit for reintroducing said withdrawn gas into said head space, thereby forming a closed sampling loop;

(f) means for causing said withdrawn gas to flow through said sampling loop; and (g) means for analyzing the oxygen concentration of said withdrawn gas flowing through said sampling loop.

DESCRIPTION OF THE INVENTION

Figure 1:
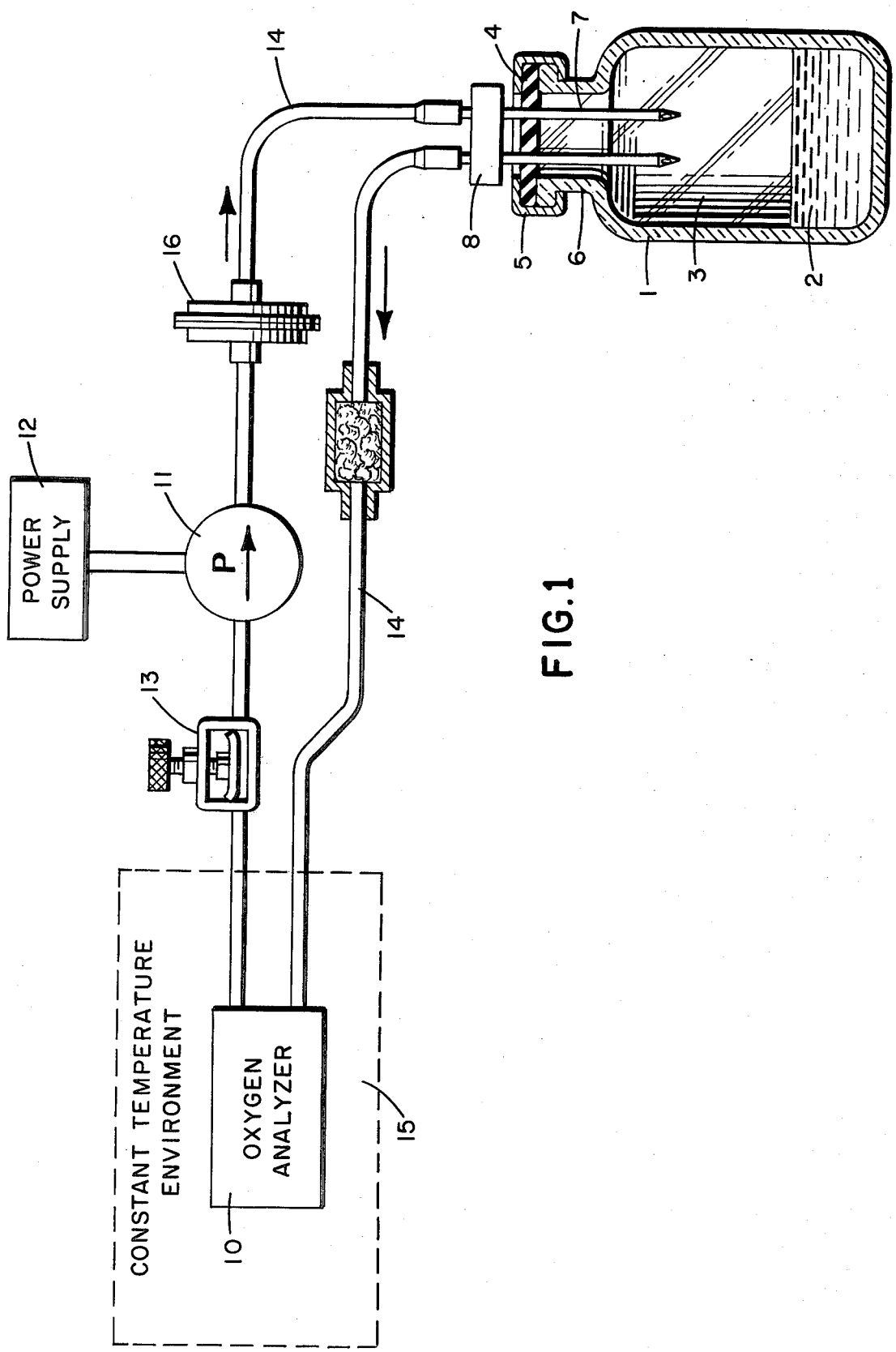
FIG. 1 shows in schematic form the apparatus of the present invention.

Most infections of the urinary tract are caused by the same gram-negative bacteria usually found in the intestine. Uncomplicated infection usually involves the Enterobacteriaceae. *E.coli* is the most common organism, being responsible for about 80% of all cases. Kalebsiella, Proteus, and Enterobacter species occur frequently, followed by Pseudomonas, Staphylococci, and Group D Streptococci, which in turn account for 5 to 10% of total adult infections. *C.albicans* and other relatively uncommon organisms may be important in the instrumented or immunosuppressed patient.

These common pathogens are facultative anaerobes or obligate aerobes; truly anaerobic organisms rarely cause urinary tract infection. Urine samples are thus usually cultured aerobically in ambient atmosphere at 35°–37° C. Whether their metabolism is oxidative or fermentative, these organisms will use oxygen as a metabolic constituent under aerobic conditions. It is the indirect measurement of this metabolically consumed oxygen which forms the basis of the present invention.

The present invention detects the presence of significant bacteriuria by monitoring consumption of oxygen in a sealed culture vial. The oxygen consumption technique is initiated by placing the urine sample to be tested in a culture medium contained in a sealable, sterile vial or container fitted with a silicone rubber septum and aluminum closure.

The growth medium employed can be any medium which will support growth of the oxygen consuming microorganisms which may be present in urine samples. These standard growth media are well known in the art. A description of suitable medium components is found in Waters U.S. Pat. No. 3,676,679 which is hereby incorporated herein by reference. Unlike the Waters media, those useful in the present invention do not require a C-14 labeled carbon source. A particularly suitable basal growth medium for use in screening urine samples for significant bacteriuria according to the present invention is tryptic soy broth (Bioquest/BBL, Cockeysville, Md.).

Introduction of the urine sample can be effected by injecting it through the septum with a hypodermic needle. Care should be taken to sterilize the needle and the septum before making the injection in order to prevent contamination of the test vial.

Immediately following inoculation, the sample vial is flushed manually with room air to replace any oxygen consumed by oxidation of the medium during autoclaving and to provide an initial reference. Measurement of the head space gas oxygen concentration is initiated by penetrating the vial septum with two hollow point needles held in a common mechanical assembly. Head space gas is removed from the vial by one needle, and is drawn through an oxygen analyzer by means of a small pump and flow constricting orifice. The analyzed gas is returned to the vial, after passage through a sterilizing filter, by the second needle. The pump is run only long enough to establish a uniform concentration of oxygen in the closed sampling loop. Freshly inoculated or sterile sample vials normally read about 20.8% $O_2$; water vapor accounts for the decrease from the 21.0% $O_2$ reading set as a calibration value when testing ambient air.

After inoculation with the test material, the inoculated vial is incubated, i.e., subjected to conditions conducive to biological activity for a predetermined period of time sufficient to result in appreciable oxygen consumption. Since most medically significant bacteria found in urine samples achieve their maximum growth rates at temperatures of approximately 36° C. plus or minus 1° C., the culture vials are desirably maintained at a temperature lying in the range from about 35° C. to about 37° C.

Agitation of the culture medium also is useful both to promote growth of biologically active agents which may be present and to facilitate a good gas-liquid exchange between the sample and the head space gas. A conventional shaking table may be utilized to effect gentle agitation. Alternatively, the culture medium can be stirred with a magnetic stirring bar magnetically coupled to a rotating magnet disposed beneath the culture vial.

During incubation, microorganisms present in the sample vial will consume dissolved oxygen from the medium, which will in turn be replenished by oxygen diffusing into the medium from the head space gas. The length of the incubation period before the oxygen concentration is again measured in the above described manner or the interval between subsequent measurements is dependent upon the chosen test protocol. Incubation intervals of about one hour are suitable for most urine screening tests. Samples containing significant numbers of bacteria will evidence head space gas oxygen content readings below the chosen threshold value (usually 20.6% $O_2$) and thus will be considered positive for significant bacteriuria in most cases within about 3 to 5 hours.

The container or vial in which the sample and medium are placed can be of any size or configuration. As described in Example 1, it has been determined that as the head space (i.e., the volume over the sample and medium) in the vial increases, the time required to detect the threshold quantities or organisms also increases. Therefore, it is preferred to keep the gas head space volume down when rapid detection is the objective. Best results have been achieved with a 20 cc (nominal) vial containing 5.0 cc growth medium and 3.0 cc inoculum which results in about 18.5 cc of head space. In general, the ratio of the amount of inoculum to the amount of medium preferably varies from about 1:2 to 1:1. For urine screening applications a 5 cc inoculum size is probably a practical upper limit. In addition, the total amount of inoculum plus medium should comprise no more than about ½ of the total vial volume. One skilled in the art will readily appreciate that the sample and head space volumes can be modified to suit any particular objective by changing the size of the vial. The shape of the vial is not critical, and in fact standard laboratory sample vials are perfectly suited to this application.

The gas phase oxygen-consumption analysis of the present invention is preferably accomplished by using a Taylor-Servomex Oxygen Analyzer, Model OA272, sold in the United States by the Taylor-Sybron Corporation, Analytical instruments Division, Rochester, N.Y. The analyzer is preferably contained in a warm air incubator maintained at 40° C. ±0.2° C. This analyzer makes use of the fact that oxygen has paramagnetic properties. The preferred paramagnetic analyzer manufactured by Servomex employs an optically coupled servomechanical feedback system.

Although the Taylor-Servomex analyzer is preferred, other gas phase oxygen analyzers, particularly those using high-temperature electrolytic cells of calcium-stabilized zirconium oxide electrolyte between porous platnum electrodes (e.g., Westinghouse Model 209) operated near 850° C. can also be used. Such analyzers produce erroneous readings when combustible gas is burned in the measurement cell, but quantities of such gas sufficient to cause appreciable error are not expected in the present application.

The details of the system for measuring head space gas oxygen content are now described in typical use discussed with reference to FIG. 1 of the drawings. A glass vial 1 containing sterile growth medium 2 and air as the head space culture gas 3 is used. The vial is fitted with self-sealing rubber septum 4 and cap 5. The septum of a vial under test is penetrated by two sterile No. 18 pencil-point needles 6 and 7 held parallel in a common mechanical assembly 8. Head space gas from the vial is removed through the first needle 6, drawn through a cotton plug 9 to remove water droplets, and then through an oxygen analyzer 10 (in a constant temperature environment 15) by means of a small displacement pump 11 powered by a variable DC power supply 12. A small pinch clamp 13 serves to restrict the gas flows through the analyzer. The sample gas is returned to the vial through a sterilizing filter 16 and then through a second needle 7, forming a closed sampling loop. All components of the sampling loop are connected with tygon tubing 14. The pump is run for a period of time sufficient to equilibrate head space gas through the sampling loop. The pump is turned off, and the vial septum additionally punctured momentarily with a sterile 18 ga. hypodermic needle to equilibrate the sampling loop pressure with that of the atmosphere. The very small quantity of ambient air admitted to or withdrawn from the vial in this step does not affect that particular analysis since the gas to be analyzed is already in the sampling loop. The effect on subsequent analysis is insignificant, especially when compared to the potential error that pressure variations might introduce into the analysis. The recorder servo and chart drives are energized to record the signal obtained from the recorder output of the oxygen analyzer. One percent $O_2$ normally corresponds to 2.0 inches chart deflection. The recorder servo and drive circuitry are then disabled and the needles removed from the vial. The pump is again energized while heat is applied to the needles from an infrared needle sterilizer (not shown). The pump and sterilizer are then turned off and the recorder again turned on in order to obtain a reference reading of the ambient air oxygen content to be used as a base line reference for testing the following vial. The recorder scale is calibrated in terms of % $O_2$ while measuring 21% $O_2$ ambient air on the 25% analyzer range. The analyzer is then switched to the 5% range, and the offset control adjusted to obtain a full-scale reading. The recorder thus spans 16 to 21% $O_2$.

The following examples are included for illustrative purposes only and are not intended to limit the scope of the invention.

EXAMPLE 1

This example demonstrates a determination of head space volume and solution volume effects upon oxygen consumption detection of bacteria using constant inoculum strength. Pairs of sterile small (20 cc nominal), medium (50 cc nominal) and large (100 cc nominal) standard 20 mm closure serum vials fitted with silicone rubber septa and aluminum caps were used in the test, prepared with sterile solutions as follows:

| | | |
|---|---|---|
| Small Vials total volume 26.5cc | S1- | 4.8cc BACTEC 6B medium[2/] 0.2cc dextrose stock, 4g/20ml 0.5cc inoculum $V_{sample}$ 5.5cc $V_{hdspc}$ 21.0cc |
| | S2- | 9.6cc BACTEC 6B medium 0.4cc dextrose stock 4g/20ml 1.0cc inoculum $V_{sample}$ 11.0cc $V_{hdspc}$ 15.5cc |
| Medium Vials total volume 64cc | M1- | 4.8cc BACTEC 6B medium 0.2cc dextrose stock 4g/20ml 0.5cc inoculum $V_{sample}$ 5.5cc $V_{hdspc}$ 58.5cc |
| | M2- | 9.6cc BACTEC 6B medium 0.4cc dextrose stock 4g/20ml 1.0cc inoculum $V_{sample}$ 11.0cc $V_{hd.spc}$ 53.0cc |
| Large Vials total volume 120cc | L1- | 4.8cc BACTEC 6B medium 0.2 dextrose stock 4g/20ml 0.5cc inoculum $V_{sample}$ 5.5cc $V_{hd.spc}$ 114.5cc |
| | L2- | 9.6cc BACTEC 6B medium 0.4cc dextrose stock 4g/20ml 1.0cc inoculum $V_{sample}$ 11.0cc $V_{hd.spc}$ 109cc |

[2/] A tryptic soy broth-based medium available from Johnston Laboratories Inc., Cockeysville, Md.

An inoculum source culture was generated using a previously prepared culture of *E. coli* in 6B medium to inoculate 9.5 cc sterile 6B medium in a 20 cc vial. The source culture was used to inoculate the various sample vials with the volumes of inoculum previously indicated. Oxygen content of the head space gas in each of the sample vials was measured immediately following inoculation. The vials were then placed in a warm air incubator at 37° C. and shaken at 250 rpm. Head space oxygen consumption was measured for each of the vials hourly for a period of 5 hours.

Figure 2:
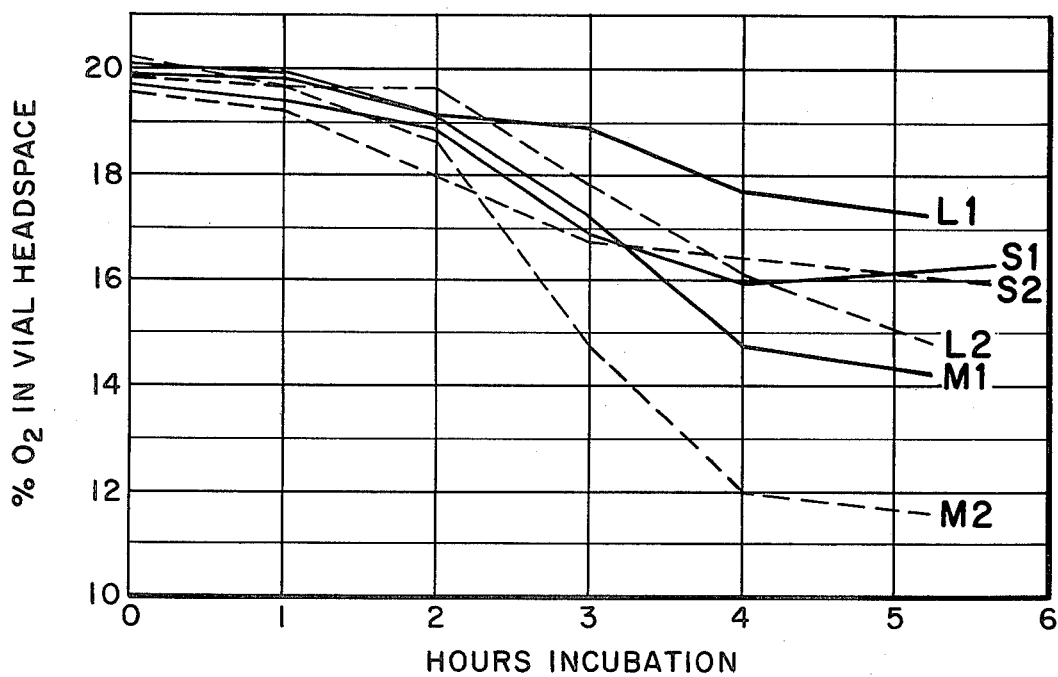
FIGS. 2 through 15 depict the results of tests demonstrating the effectiveness of the present invention.

Oxygen consumption as a function of incubation time is presented in FIG. 2. The time required for each of the vials to exhibit 19% head space oxygen content using ambient air as reference is listed in Table 1.

Table 1

| Oxygen Consumption Detection Time Variation with Vial Head Space and Solution Volume at Constant Inoculum Strength | | |
|---|---|---|
| Sample Vial | | Time-to-Detection |
| ID | Sltn. Vol. | Hd. Spc. Vol. | Hours (19% $O_2$) |
| S1 | 5.5cc | 21.0cc | 1.8 |
| S2 | 11.0cc | 15.5cc | 1.2 |
| M1 | 5.5cc | 58.5cc | 2.1 |
| M2 | 11.0cc | 53.0cc | 1.6 |
| L1 | 5.5cc | 114.5cc | 2.8 |
| L2 | 11.0cc | 109.0cc | 2.4 |

Considering either the series (S1, M1, L1) or the series (S2, M2, L2) it may be noted that increasing the head space volume also increases the time required to detect organism growth. Contrasting the above two series, it may be seen that detection time decreases as the absolute number of organisms in each vial increases, best exemplified by the large vial (L1, L2) results, where total solution volume remains less than 10% of the total vial volume in both cases. Refering to FIG. 2, it is observed that S1 and S2 vials detect first, but that the total amount of oxygen consumed at the end of the test is greater for the medium (M1, M2) vials. Large vial detection is considerably delayed. If it is assumed that oxygen is consumed from the head space gas at the same rate for the same number of bacteria present in a given vial, these results may be readily explained. Small vials contain less oxygen by virtue of their reduced head space volume; a given quantity of oxygen consumed by the organism thus represents a larger percentage of available oxygen, resulting in more rapid detection. Increasing the total number of organisms in the vial increases the consumption rate, accelerating the process. Because the head space volume for the small vial and the volume of the remainder of the sampling loop are similar, a steady-state is approached when the growth-limited concentration of organisms is reached wherein a substantial portion of the measured head space oxygen content is supplied by the ambient air purge of the sampling loop. The use of small sample vials, then, decreases the time required for detection at the expense of maximum indicated oxygen consumption in the long-incubation limit. Medium and large vial results may be explained by logical extension of the above arguments. Maximum utilization of oxygen is of secondary interest if the system is to be used for the rapid detection of bacteriuria.

EXAMPLE 2

This example demonstrates the detection and quantification of *E. coli* in the process of the present invention.

Sterile 20 cc vials were prepared containing 5.0 cc of the following growth medium:
2.5 cc BACTEC 6B medium
2.0 cc deionized water
0.5 cc 4.5 g/20 cc dextrose stock solution in deionized water A previously prepared culture of *E. coli* was used to inoculate 10 cc of refrigerated clean-caught urine. The culture was added dropwise via a hypodermic syringe until visual turbidity was achieved; several additional drops were then added. The urine source culture was then incubated at 37° C. for 2 hours. Three vials containing 9.0 cc refrigerated urine were also prepared; the test was initiated by removing 1.0 cc of the incubated source culture, and performing serial dilutions with the three urine vials. Four oxygen consumption vials were inoculated by syringe with 3.0 cc for each of the four culture concentrations, now in ratios of 1:1, 1:10, 1:100 and 1:1000.

Figure 3:
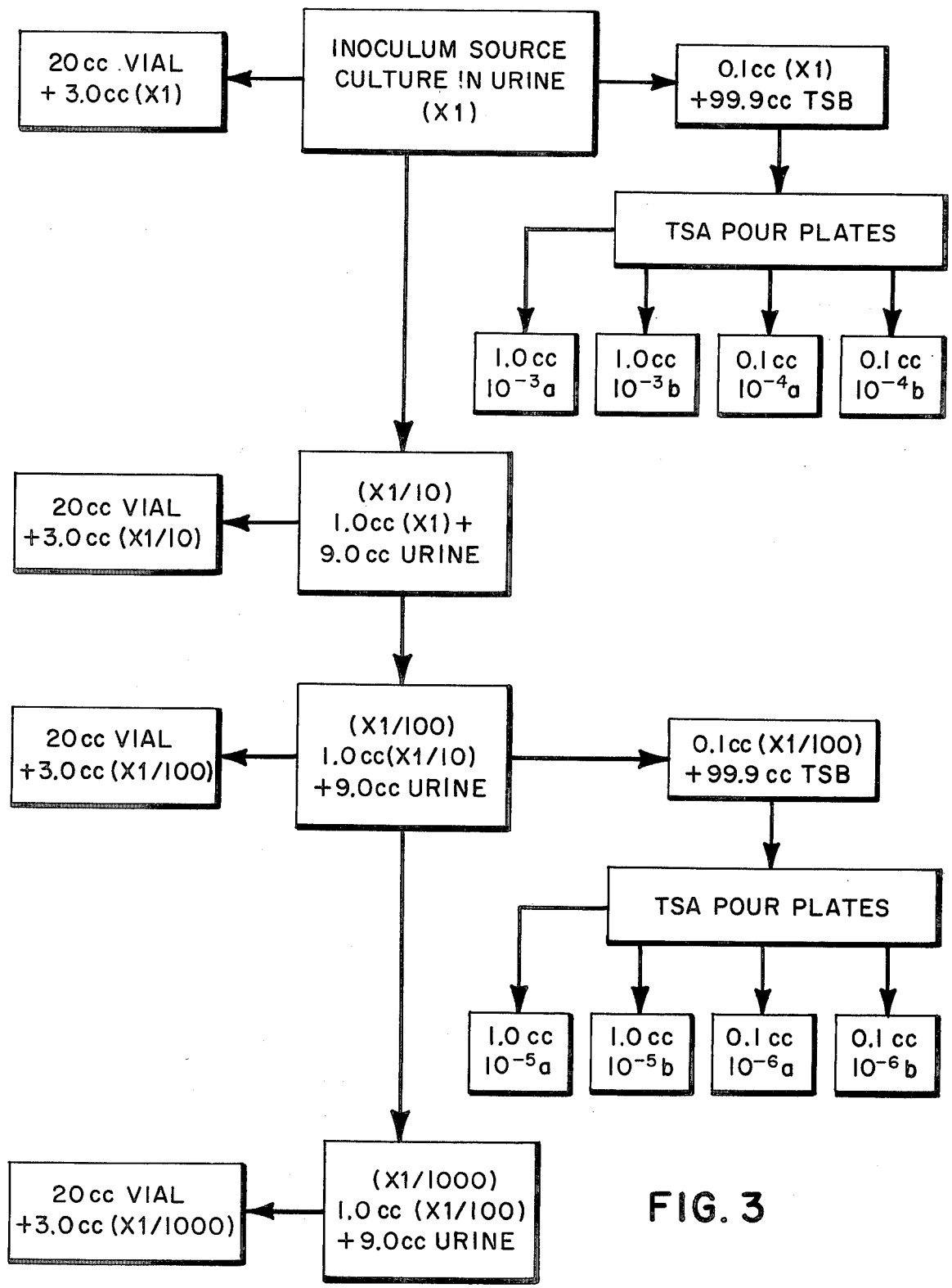

A parallel BACTEC (radiometric $C^{14}O_2$ detection) test was performed. Tryptic soy agar (BBL, Cockeysville, Md.) pour plates (40 g/l) were employed for absolute quantitation. 0.1 cc of the source culture (1:1) was diluted in 99.9 cc refrigerated tryptic soy broth (27.5 g/l). Duplicate plates were prepared using 1.0 cc and 0.1 cc samples from the tryptic soy broth dilution vial, giving $10^3$ and $10^4$ dilutions of the source culture. Similarly, 0.1 cc was withdrawn from the 1:100 urine dilution vial and was added to a second refrigerated vial containing 99.9 cc tryptic soy broth to prepare duplicate plates at $1:10^5$ and $1:10^6$ dilution ratios. All plates were poured using 10-15 ml tryptic soy agar at 45° C., allowed to set, and then incubated overnight at 37° C. This sampling and dilution scheme, common to all the remaining examples, is presented schematically in FIG. 3.

Inoculated vials for oxygen consumption study were purged with 100 cc of ambient air and read initially immediately following the inoculation of all sample vials. These vials were then placed in a warm air incubator at 37° C. with 250 rpm agitation. The tryptic soy agar plates were thus prepared following the initial reading period; refrigeration of the dilution vials before sampling was used to inhibit further growth of the organism.

Oxygen consumption readings were obtained hourly using the sampling scheme discussed with respect to FIG. 1.

Figure 4:
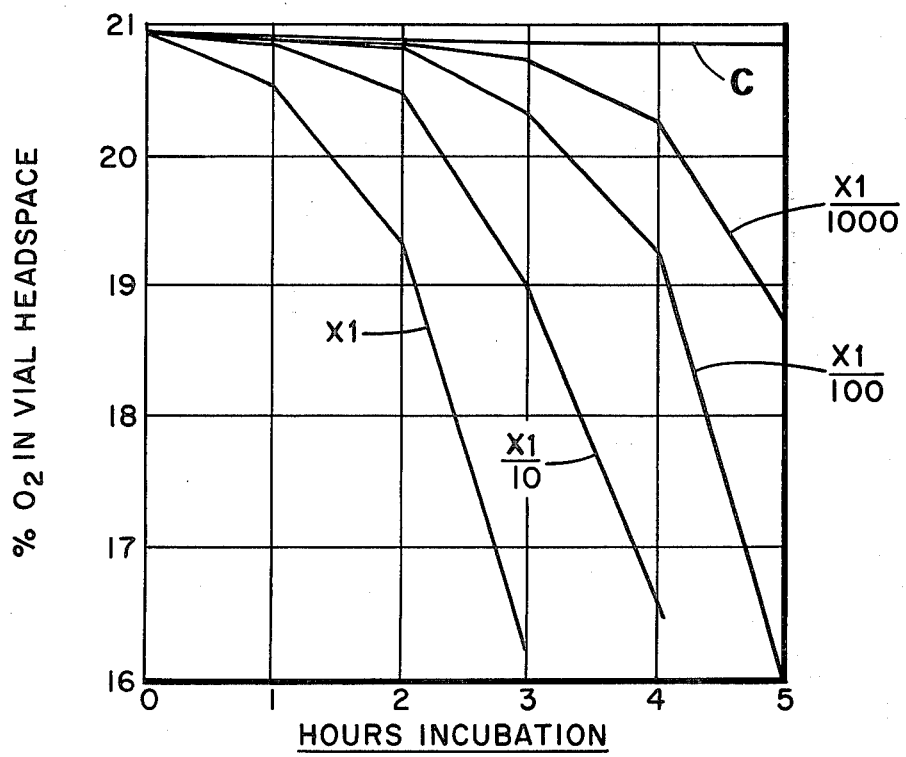
Figure 5:
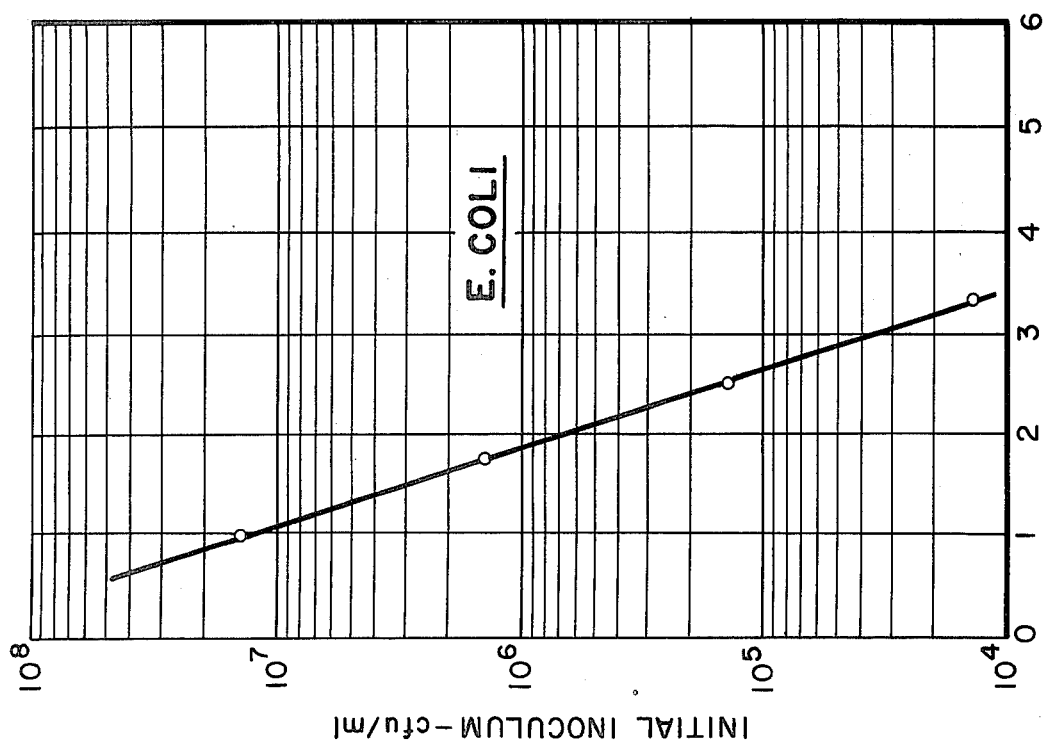

Results of the test are presented in FIG. 4. *E. coli* is observed to readily consume oxygen from the head space gas. Serial dilutions of the inoculum are shown to detect at the 20.6% $O_2$ level at times linearly and inversely proportional to the logarithm of the actual inoculum concentration, as more clearly depicted in FIG. 5. Pour plate results for this test indicate the initial (x1) inoculum contained $1.4 \times 10^7$ cfu/ml *E. coli*, detected in 1 hour.

EXAMPLE 3

This example demonstrates the detection and quantification of *E. cloacae*.

Sterile 20 cc vials were prepared containing 5.0 cc of medium as detailed for the *E. coli* test. A 0.2 cc sample of a previously prepared culture of *E. cloacae* in 6B BACTEC medium was used to inoculate 10 cc refrigerated urine as a source culture. Following incubation at 37° C. and 250 rpm for 1.5 hours, the dilution and sampling scheme described in FIG. 3 was implemented to prepare serially diluted inocula and sample vials for oxygen consumption and parallel BACTEC determinations. Tryptic soy agar pour plates were again prepared. Readings of head space gas oxygen content were recorded hourly.

Figure 7:
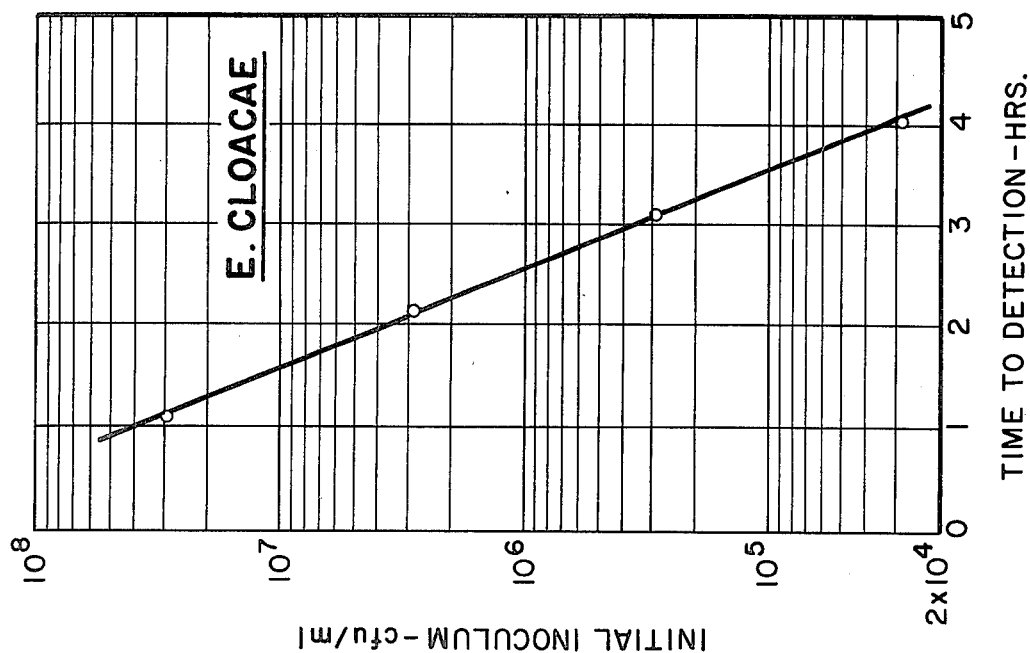
Figure 6:
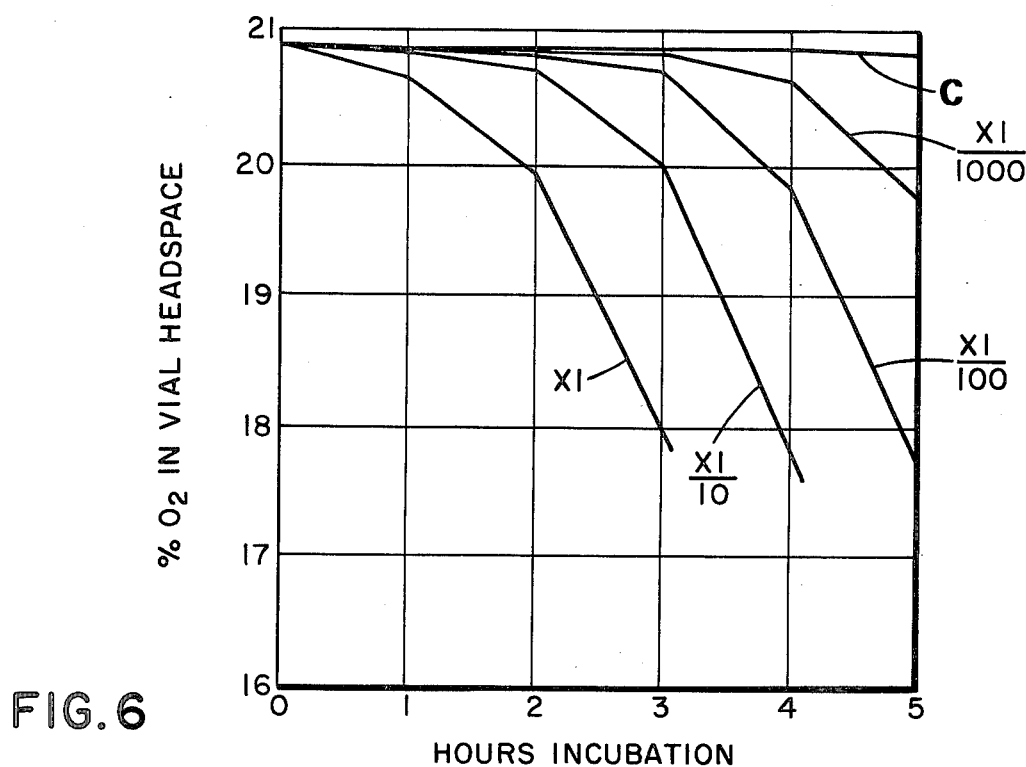

Results of the oxygen consumption test are presented in FIG. 6. *E. cloacae* readily consumes oxygen from the head space gas, reducing the head space oxygen content to 20.6% in 1.1 hours incubation time for an initial (x1) inoculum of $2.9 \times 10^7$ cfu/ml as determined by 24-hour pour plate counts. Time-to-detection as a function of the logarithm of initial inoculum is presented in FIG. 7.

EXAMPLE 4

This example demonstrates the detection of quantification of *P. mirabilis*.

Sterile 20 cc vials containing 5.0 cc growth medium were prepared as for the *E. coli* and *E. cloacae* tests. The inoculum source culture was generated using 0.2 cc of a previously prepared culture of *P. mirabilis* in BACTEC 6B medium to inoculate 10 cc refrigerated urine, followed by incubation of the urine culture for 1.5 hours at 37° C. with 250 rpm reciprocation. The test was initiated using the sampling and dilution scheme outlined in FIG. 3 to prepare serially diluted inocula and associated sample vials for oxygen consumption and parallel BACTEC determinations. Tryptic soy agar pour plates were likewise prepared for overnight incubation. All sample vials were agitated at 250 rpm with 37° C. incubation during the course of the test. Head space gas oxygen content was sampled and recorded hourly. The test was continued for 5 hours.

Figure 8:
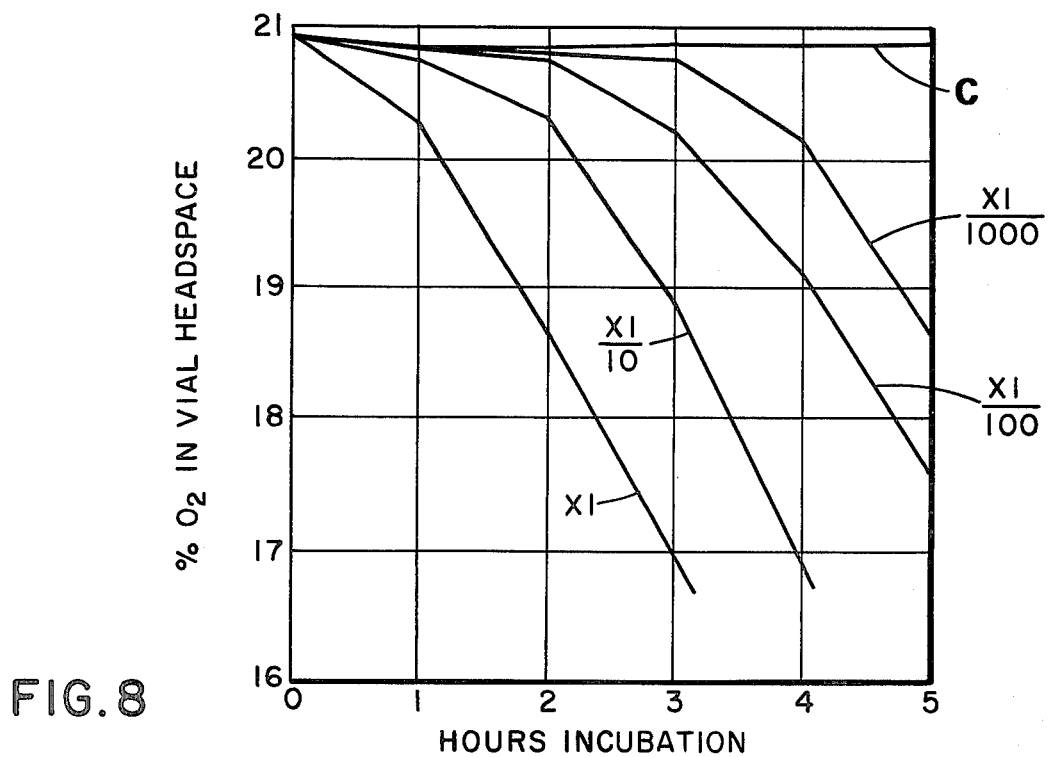
Figure 9:
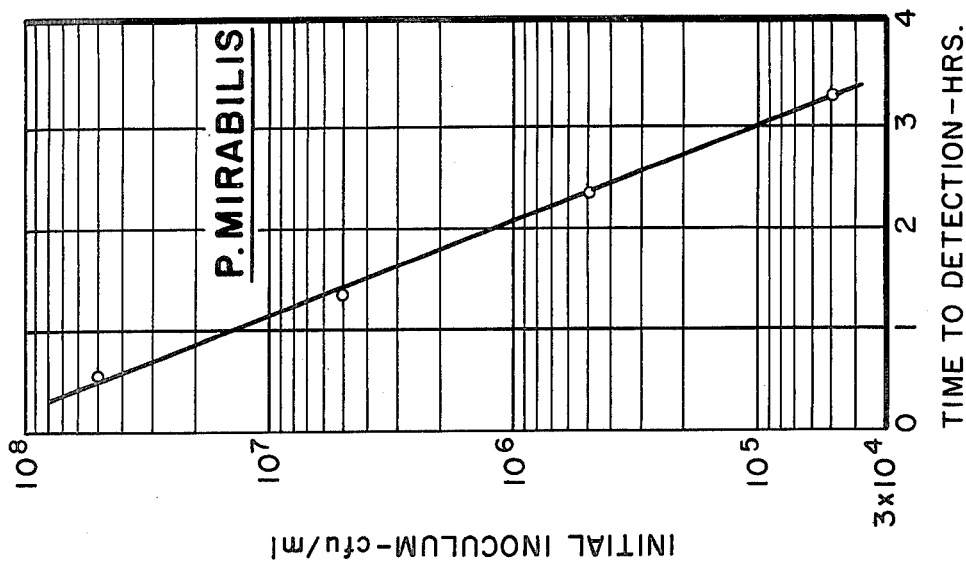

Oxygen consumption by *P. mirabilis* as a function of incubation time is presented graphically in FIG. 8. As with *E. coli* and *E. cloacae*, *P. mirabilis* readily consumes oxygen from the head space gas, resulting in detection at the 20.6% level in 0.5 hours for an initial (x1) inoculum of $5.0 \times 10^7$ cfu/ml as determined by the pour plate technique. Time-to-detection as a function of the logarithm of initial inoculum is presented in FIG. 9.

EXAMPLE 5

This example demonstrates the detection and quantification of *P. aeruginosa*.

Sterile 20 cc vials were prepared containing 5.0 cc of the growth medium described in Example 2. 0.4 cc of an overnight culture of *P. aeruginosa* grown in urine was used to inoculate 9.0 cc refrigerated urine. This source culture was then sampled and serially diluted as per FIG. 3 to prepare sample vials for the oxygen consumption and parallel BACTEC determinations. Tryptic soy agar pour plates were also prepared for overnight incubation. Readings of head space gas oxygen content were recorded hourly. The test was continued for 5 hours.

Figure 11:
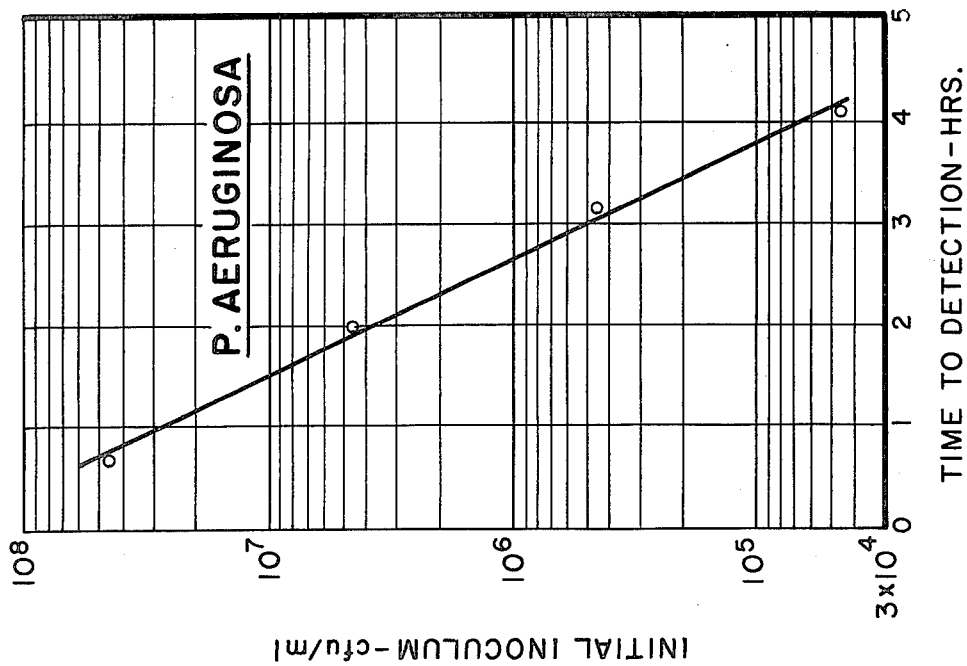
Figure 10:
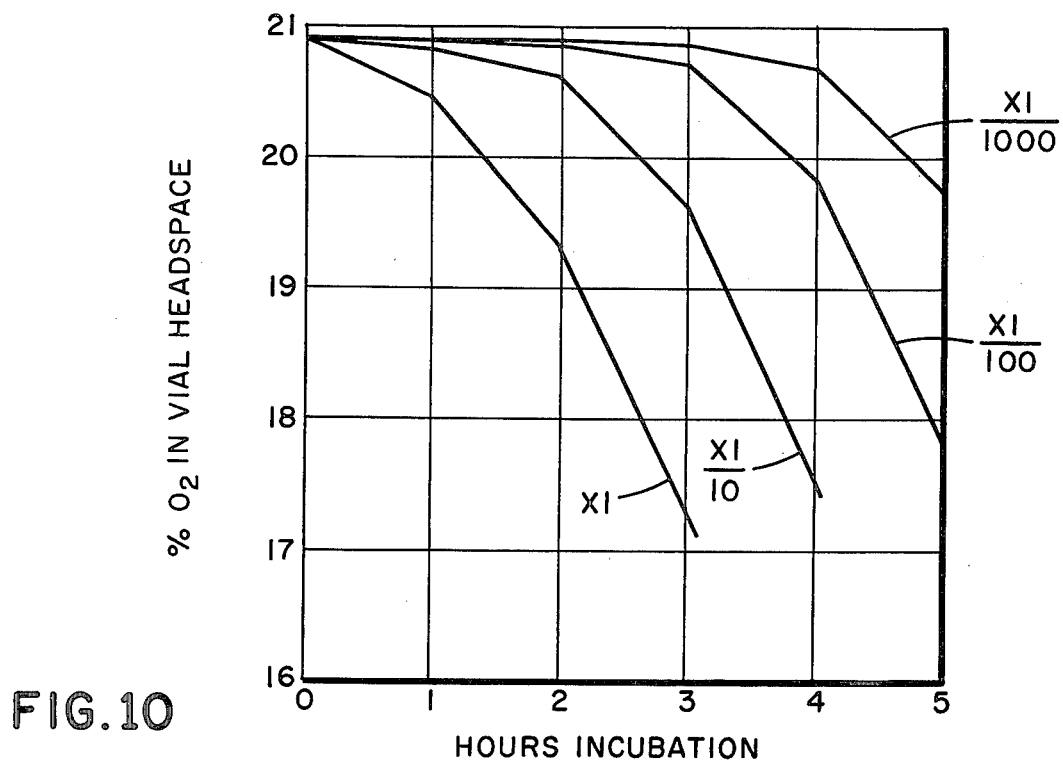

Results of the oxygen consumption test are presented in FIG. 10. Presence of the organism is detected by reduction of the head space oxygen content to 20.6% at 0.8 hours incubation at 37° C. with 250 rpm reciprocation for an initial (x1) inoculum of $4.5 \times 10^7$ cfu/ml as determined by 24-hour plate count. Time-to-detection is related to the logarithm of initial inoculum in FIG. 11.

EXAMPLE 6

This example demonstrates the detection and quantification of *S. aureus*.

Sterile 20 cc vials containing 5.0 cc growth medium as used in Example 2 were prepared for oxygen consumption investigation. A culture of *S. aureus* in urine incubated overnight at 37° C. was diluted 1:10 in previously refrigerated urine to generate the inoculum source culture. The dilution and sampling scheme described in FIG. 3 was implemented to prepare serially diluted inocula and sample vials for oxygen consumption and parallel BACTEC determinations. Tryptic soy agar pour plates were also prepared. All sample vials were incubated at 37° C. with 250 rpm agitation. Readings of head space gas oxygen content were recorded hourly. The progress of the test was followed for 6 hours.

Figure 12:
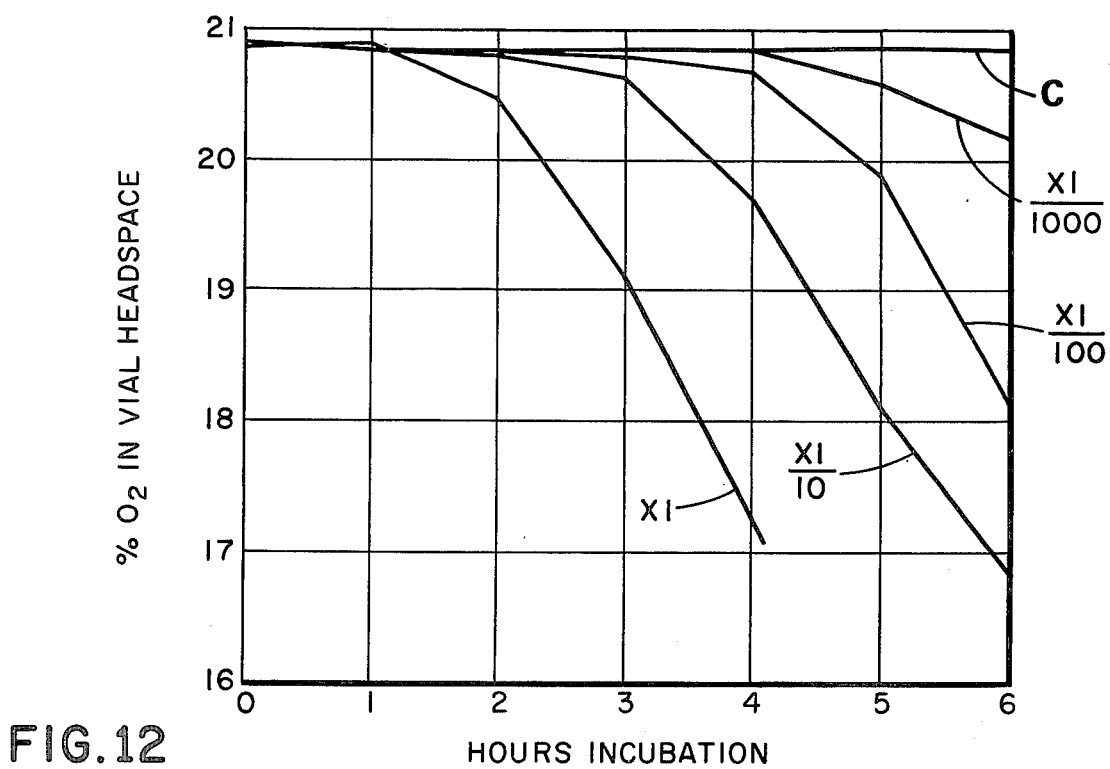
Figure 13:
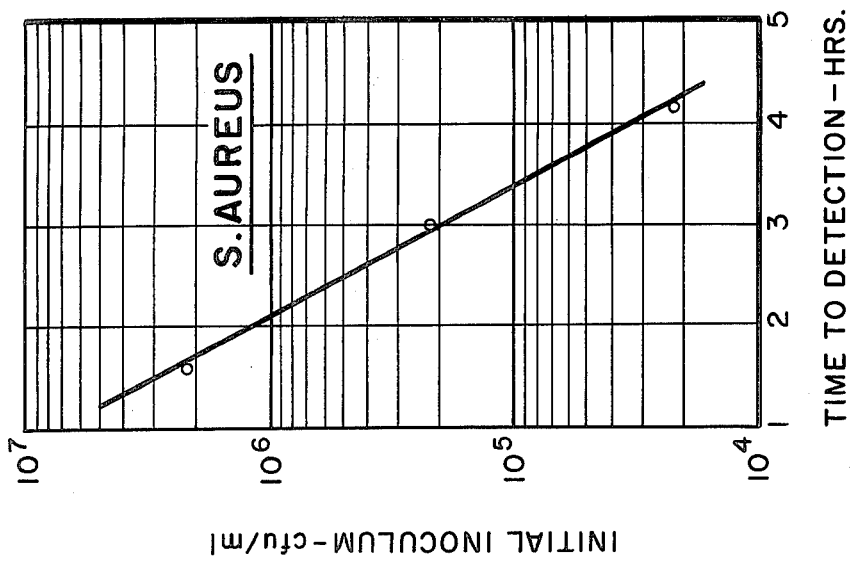

Oxygen consumption data for *S. aureus* is shown in FIG. 12. Head space gas oxygen concentration is reduced to the 20.6% detection threshold in 1.6 hours for an initial inoculum containing $2.2 \times 10^6$ cfu/ml as determined by the 24-hour pour plate results. Time-to-detection as a function of the logarithm of initial inoculum is presented in FIG. 13.

EXAMPLE 7

This example demonstrates the detection and quantification of *C. albicans*.

5.0 cc dextrose-enriched growth medium in 20 cc sterile vials was prepared as in Example 2. 0.5 cc of an overnight culture of *C. albicans* in dextrose-enriched 6B medium was added to 9.0 cc refrigerated urine to prepare the inoculum source culture. The source culture was diluted and sample vials for oxygen consumption and parallel BACTEC tests prepared with reference to FIG. 3. Tryptic soy agar pour plates were similarly prepared for overnight incubation. All sample vials were incubated at 37° C. with 250 rpm reciprocation. Readings of head space gas oxygen content were recorded at hourly intervals. The test was continued for 8 hours.

Figure 15:
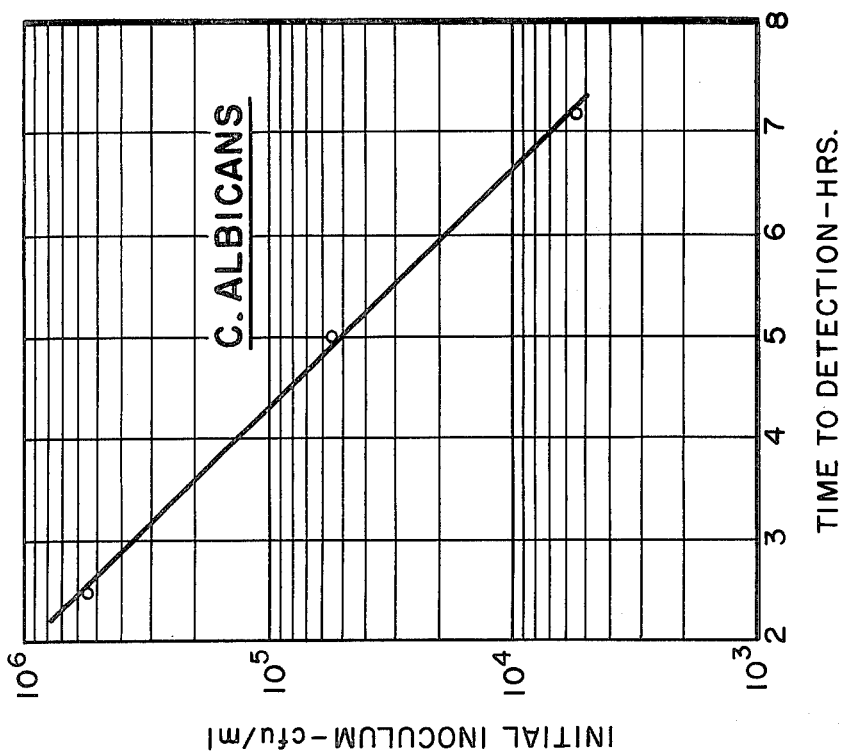
Figure 14:
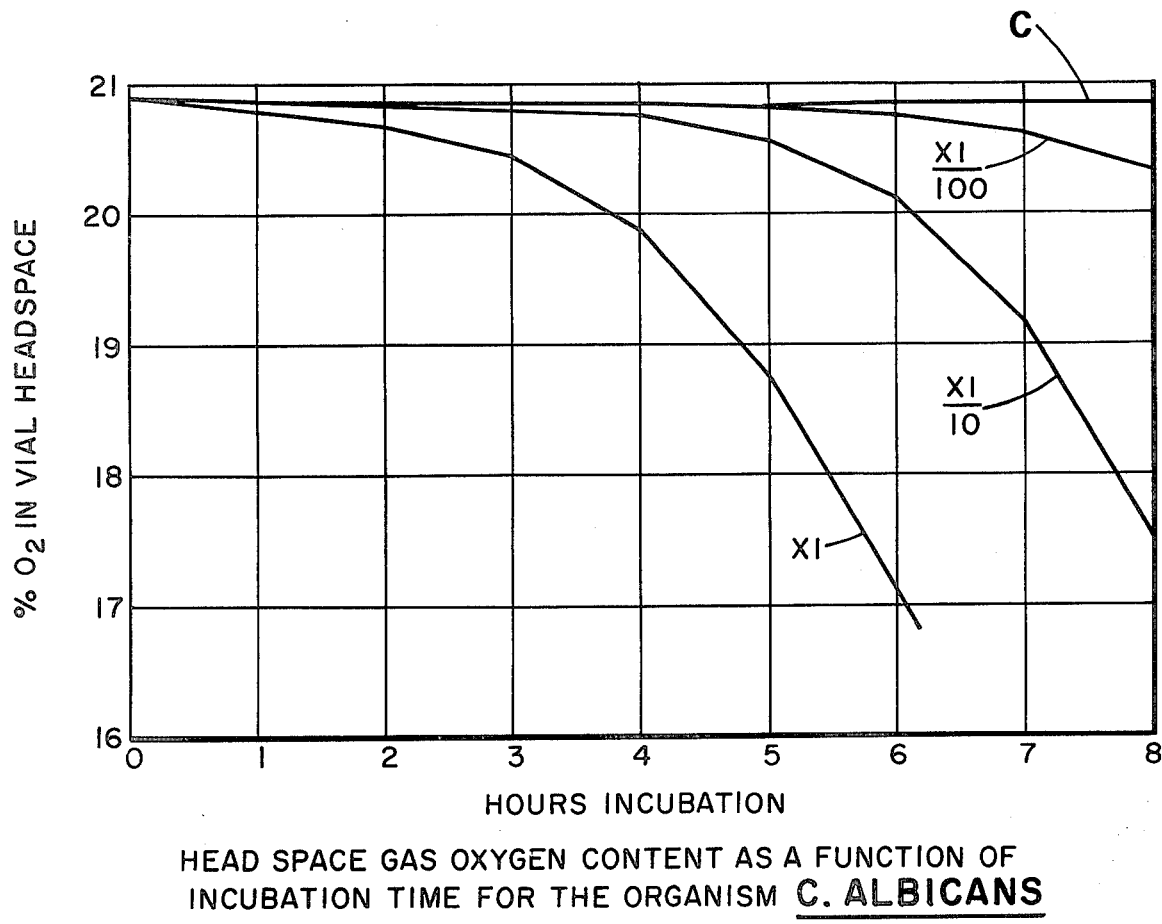

Sample vial head space oxygen content as a function of incubation time is shown in FIG. 14. Metabolism of *C. albicans* is detected by oxygen utilization at the 20.6% level at 2.5 hours incubation time for an initial (x1) inoculum of $5.5 \times 10^5$ cfu/ml as determined by the pour plate technique. Time-to-detection as a function of the logarithm of initial inoculum is presented in FIG. 15. Only three values are plotted; the somewhat lower than usual initial inocula, coupled with the slow growth of *C. albicans* precluded the detection of the final (x1/1000) serial dilution vial.

The common urinary tract pathogens tested in the above examples were all detected with good quantification using the head space gas oxygen consumption technique. The members of the Enterobacteriaceae (*E. coli, E. cloacae, P. mirabilis*) grew and detected most rapidly. In the parallel radiometric tests (BACTEC), some organisms were detected somewhat earlier (1–2 hrs) while others were detected later (1–2 hrs) than the oxygen consumption tests.

The incubation times necessary to provide oxygen consumption detection of a $10^5$ cfu/ml of each of the tested organisms is presented in Table 2. An incubation period of 3 to 5 hours would appear adequate to detect the majority of true positive samples while providing time to perform further handling and testing of such positives before the end of the work-day, assuming midmorning inoculation.

Table 2

Times-to-Detection for $10^5$ cfu/ml Inoculum of Various Organisms Studied by Head Space Gas Oxygen Consumption

| Organism | Time-to-Detection Hours, $10^5$ cfu/ml Inoculum |
|---|---|
| E. coli | 2.7 |
| E. cloacae | 3.5 |
| P. mirabilis | 3.0 |
| P. aeruginosa | 3.8 |
| S. aureus | 3.4 |
| C. albicans | 4.4 |

EXAMPLE 8

This example demonstrates a clinical trial of the oxygen consumption technique of the present invention for the detection of significant bacteriuria. The test was conducted in conjunction with Sinai Hospital of Baltimore over a 38-day perod. During this period 297 urine samples were collected from Sinai and tested at Johnston Laboratories using the oxygen consumption technique in parallel with the BACTEC system. Tryptic soy agar pour plates were employed to check actual organism counts.

The test was carried out as follows. 3.0 cc of each urine sample was injected via sterile syringe into specially prepared 20 cc vials containing 5.0 cc growth medium (based on tryptic soy broth) for the oxygen consumption ($O_2$) study; a similar vial was inoculated with 3.0 cc sterile deionized water to serve as the daily $O_2$ control. 0.1 cc of each urine was injected into a previously refrigerated 100 cc vial containing 100 cc ½-strength tryptic soy broth without dextrose to obtain a 1,000:1 dilution. Sample and reference vials for the $O_2$ study were then flushed with 100 cc ambient air and read to obtain initial oxygen concentration. All vials were then placed in a warm-air incubator at 37° C. and agitated with reciprocation at 250 rpm on an NBS Model R-2 shaker. Pour plates for each sample at 1,000:1 and 10,000:1 dilutions were then prepared using 1.0 cc and 0.1 cc respectively, transferred by sterile syringe from each dilution vial per 10–15 ml tryptic soy agar. All plates were incubated at 36° C. and read after 24 hours. Oxygen consumption readings were obtained hourly for a period of four hours.

Of the 297 samples collected, 12 were omitted from the test for various reasons (e.g., incomplete hospital data). The remaining 285 samples on which the tests were based samples included 85 (29.8%) considered significant and 200 (70.2%) considered nonsignificant. Table 3 lists the organisms identified by Sinai Hospital in the significant samples. The number of samples containing each organism is also noted, as is the percentage of the total containing that organism. The fractional sample numbers are due to mixed organism specimens. Two samples containing more than 3 organisms are omitted from the table.

Table 3

| Organisms Contributing to Significant Samples | | |
|---|---|---|
| Organism | Number of Samples | Percentage |
| E. coli | 44 5/6 | 54.0% |
| P. mirabilis | 15 | 18.1 |
| P. aeruginosa | 6½ | 7.6 |
| K. pneumoniae | 5 1/6 | 6.2 |
| Group D. Strep | 4½ | 5.2 |
| S. albus | 2½ | 3.0 |
| P. morganii | 1⅔ | 2.0 |
| S. marcescens | 1 | 1.2 |
| S. liquifaciens | ½ | 0.6 |
| Group B Strep | ½ | 0.6 |
| Herellea | ½ | 0.6 |
| S. aureus | ⅓ | 0.4 |
| C. diversus | ⅓ | 0.4 |
| | 83 | 99.9% |

Results of the test for the 285 samples considered for data analysis are set out in Table 4.

Table 4

| | $O_2$ Consumption |
|---|---|
| True Positive: | 79 (27.7%) |
| True Negative: | 193 (67.7%) |
| False Positive: | 7 (2.5%) |
| False Negative: | 6 (2.1%) |
| | 285 (100.0%) |

The oxygen consumption technique of the present invention detected 92.9% of urines considered significant in the study, yielding a total sample false negative rate of 2.1%, with a 2.5% false positive rate. The parallel BACTEC tests provided essentially equivalent results.

The oxygen consumption technique of the present invention is shown to provide competent detection of significant bacteriuria, with clinically acceptable levels of false negative and false positive results. The rapidity and sensitivity of the method compare favorably with the parallel results obtained using the BACTEC system.

While certain specific embodiments of the invention have been described with particularity herein, it should be recognized that various modifications thereof will occur to those skilled in the art. Therefore, the scope of the invention is to be limited solely by the scope of the claims appended hereto.

I claim:

1. A method of detecting a threshold quantity of oxygen consuming microorganisms in a urine sample comprising the steps of:

(a) providing a sealable, sterile container containing a sterile culture medium capable of supporting growth of microorganism found in urine samples;
    (b) introducing a sample to be tested into said container, and sealing said container, the volume above said sample and medium defining a head space, and the gas initially filling this head space having a known oxygen concentration;
    (c) subjecting said sealed container and its contents to conditions conducive to microorganism growth for a period of time sufficient for the growth of oxygen consuming microorganisms;
    (d) withdrawing a portion of the head space gas from said container and causing the withdrawn gas to flow through a closed sampling loop which returns the withdrawn gas to the head space in the container; and
    (e) subjecting the gas flowing through the closed sampling loop to analysis for oxygen concentration, a drop in oxygen concentration below a predetermined level indicating the presence of a threshold quantity of said oxygen consuming microorganisms.

2. The method of claim 1 wherein said container is provided with a self-sealing rubber septum.

3. The method of claim 2 wherein said urine sample is introduced into said container by injecting said sample through said septum with a hypodermic syringe.

4. The method of claim 2 wherein said head space gas is withdrawn from said container through a first sterile hollow needle inserted through said septum.

5. The method of claim 4 wherein said head space gas is returned to said container through a second sterile, hollow needle inserted through said septum.

6. The method of claim 5 wherein said first and second hollow needles are carried on a common mechanical assembly for simultaneous penetration of said septum.

7. The method of claim 1 wherein said gas initially filling the container head space is air.

8. The method of claim 1 wherein said container and its contents are subjected to conditions conducive to microorganism growth by maintaining said container at a temperature of about 35° to 37° C.

9. The method of claim 1 wherein said culture medium in said container is agitated during the period of time the container and its contents are subjected to conditions conducive to microorganism growth.

10. The method of claim 9 wherein said agitation is effected by gently shaking said container.

11. The method of claim 9 wherein said agitation is effected by a magnetic stirring bar in said container, said stirring bar being subjected to the field of a rotating magnet outside said container.

12. The method of claim 1 wherein during the period of time in which said container and its contents are subjected to conditions conducive to microorganism growth, said head space gas is repeatedly sampled and analyzed at periodic intervals.

13. The method of claim 1 wherein said predetermined oxygen concentration level is 20.6% $O_2$ by volume.

14. The method of claim 1 wherein the oxygen concentration of the gas initially filling said head space is determined by the sampling and analysis procedures of steps (d) and (e).

15. The method of claim 1 wherein said withdrawn head space gas is analyzed in a paramagnetic oxygen analyzer.

16. The method of claim 1 wherein said analysis for oxygen concentration is begun after said withdrawn gas has been caused to flow through said closed sampling loop for a period of time sufficient to equilibrate in composition with the gas in said head space.

17. The method of claim 1 wherein said withdrawn gas is caused to flow through said closed sampling loop by a pump disposed in said loop.

18. The method of claim 1 wherein said analysis for oxygen concentration is effected in a temperature controlled environment.

19. The method of claim 18 wherein said analysis is effected in an environment maintained at about 40° C.

20. A method for testing urine samples for significant bacteriuria comprising the steps of:
 (a) providing a sealable, sterile container containing a sterile culture medium capable of supporting growth of bacteria found in urine samples;
 (b) introducing a urine sample into said container and sealing said container, the volume above said sample and medium defining a head space;
 (c) initially determining the oxygen concentration of the gas filling said head space;
 (d) subjecting said sealed container and its contents to conditions conducive to bacterial growth for a period of time sufficient for the consumption of oxygen by said bacteria;
 (e) at repeated periodic intervals during the time period of step (d):
  (i) withdrawing a portion of head space gas from said container and causing said withdrawn gas to flow through a closed sampling loop which returns said withdrawn gas to the head space in said container, and
  (ii) subjecting the gas flowing through said closed sampling loop to analysis for oxygen concentration; and
 (f) monitoring said repeated, periodic analyses of head space gas oxygen concentration for a drop in oxygen concentration to a predetermined level indicating the presence of significant bacteriuria.

21. Apparatus for detecting a threshold quantity oxygen consuming microorganisms in a urine sample comprising:
 (a) a sealable, sterile container adapted to hold in a lower portion thereof a sample of material to be tested and a culture medium which will support growth of the microorganism to be detected, said container also having an upper portion defining a head space for holding gas in contact with said sample and medium, said container further provided with means through which said sample can be introduced into said container;
 (b) means for subjecting said container and its contents to conditions conducive to microroganism growth;
 (c) means for withdrawing gas from the head space in said container;
 (d) a sampling conduit communicating with said means for withdrawing gas;
 (e) means communicating with said sampling conduit for reintroducing said withdrawn gas into said head space, thereby forming a closed sampling loop;
 (f) means for causing said withdrawn gas to flow through said sampling loop; and
 (g) means for analyzing the oxygen concentration of said withdrawn gas flowing through said sampling loop.

22. The apparatus of claim 21 wherein said means through which said sample can be introduced is a self-sealing rubber septum.

23. The apparatus of claim 22 wherein said means for withdrawing gas and said means for reintroducing withdrawn gas comprise a pair of sterile, hollow needles positioned on a common mechanical assembly, said assembly being movable for simultaneous penetration of said septum by said needles.

24. The apparatus of claim 21 wherein said means for subjecting said container and its contents to conditions conducive to microorganism growth comprises an incubator.

25. The apparatus of claim 24 wherein said incubator is additionally provided with associated means for agitating said culture medium.

26. The apparatus of claim 21 wherein said means for causing said withdrawn gas to flow through said sampling loop comprises a pump.

27. The apparatus of claim 21 wherein said means for analyzing comprses a paramagnetic oxygen analyzer.

28. The apparatus of claim 27 additionally comprising means for maintaining said paramagnetic oxygen analyzer in a controlled temperature environment.

* * * * *